(12) United States Patent
Zoughi et al.

(10) Patent No.: US 7,190,177 B2
(45) Date of Patent: Mar. 13, 2007

(54) METHOD AND APPARATUS FOR NONDESTRUCTIVE SAMPLE INSPECTION

(75) Inventors: Reza Zoughi, Wildwood, MO (US); Sergiy Kharkivskiy, Rolla, MO (US); Mohammad Tayeb Ahmad Ghasr, Rolla, MO (US)

(73) Assignee: The Curators of the University of Missouri, Columbia, MO (US)

( * ) Notice: Subject to any disclaimer, the term of this patent is extended or adjusted under 35 U.S.C. 154(b) by 135 days.

(21) Appl. No.: 10/920,723

(22) Filed: Aug. 18, 2004

(65) Prior Publication Data

US 2006/0039257 A1 Feb. 23, 2006

(51) Int. Cl.
*G01R 27/32* (2006.01)
(52) U.S. Cl. .................... 324/642; 324/763; 324/765
(58) Field of Classification Search ............ 324/642, 324/765–766, 763–764
See application file for complete search history.

(56) References Cited

U.S. PATENT DOCUMENTS

| 4,286,216 | A | | 8/1981 | Auld et al. ................ 324/237 |
|---|---|---|---|---|
| 4,364,012 | A | * | 12/1982 | Auld ........................ 324/237 |
| 5,216,372 | A | | 6/1993 | Zoughi et al. ............. 324/644 |
| 5,384,543 | A | * | 1/1995 | Bible et al. ................ 324/644 |
| 5,438,276 | A | * | 8/1995 | Kawata et al. ............. 324/765 |
| 5,440,238 | A | | 8/1995 | Martens et al. ............ 324/636 |
| 5,701,083 | A | * | 12/1997 | Goldberg et al. .......... 324/642 |
| 5,748,003 | A | | 5/1998 | Zoughi et al. ............. 324/644 |
| 5,847,573 | A | * | 12/1998 | How et al. ................. 324/765 |
| 5,859,535 | A | | 1/1999 | Liu ........................... 324/632 |
| 6,100,703 | A | | 8/2000 | Davidov et al. ........... 324/631 |
| 6,359,446 | B1 | | 3/2002 | Little, Jr. ................... 324/637 |
| 6,426,644 | B1 | * | 7/2002 | Borden et al. ............. 324/765 |
| 6,462,561 | B1 | | 10/2002 | Bigelow et al. ........... 324/637 |
| 6,512,385 | B1 | * | 1/2003 | Pfaff et al. ................. 324/753 |
| 6,538,454 | B1 | | 3/2003 | Frenkel et al. ............. 324/637 |
| 6,639,393 | B2 | * | 10/2003 | Tasker et al. ............ 324/76.19 |
| 6,819,120 | B2 | * | 11/2004 | Tam .......................... 324/633 |

OTHER PUBLICATIONS

D. Hughes, N. Wang, T. Case, K. Donnel, and R. Zoughi, "Microwave Nondestructive Detection of Corrosion Under thin Paint and Primer in Aluminum Panels," Subsurface Sensing Technologies and Applications, vol. 2, N4, Oct. 2001.

D. Hughes, R. Zoughi, R. Austin, N. Wood, and R. Engelbart, "Near-Field Microwave Detection of Corrosion Precursor Pitting Under Thin Dielectric Coatings in Metallic Substrate," Review of progress in Quantitative Nondestructive Evaluation, vol. 22, ed.by D.O. Thompson and D.E. Chimenti, Belingham, Washington, 2002, p. 462-469.

* cited by examiner

*Primary Examiner*—Andrew H. Hirshfeld
*Assistant Examiner*—Marina Kramskaya
(74) *Attorney, Agent, or Firm*—Greer, Burns & Crain, Ltd.

(57) ABSTRACT

An apparatus for inspecting a sample for defects includes a signal generator for generating a signal and a device for splitting the signal into two separate signals which have substantially equal phase and magnitude. A sensor radiates the two signals on the sample and receives the two signals reflected from the sample. A device is provided for determining a difference between the two signals reflected from the sample without unwanted influence of variations of distance between the sensor and sample, and reflections from nearby sample edges and boundaries. A defect is determined to exist when a difference is found between the two reflected signals.

38 Claims, 6 Drawing Sheets

METHOD AND APPARATUS FOR NONDESTRUCTIVE SAMPLE INSPECTION

STATEMENT OF GOVERNMENT INTEREST

This invention was made with Government assistance under Air Force Contract No. F33615-02-C5705. The Government has certain rights in this invention.

FIELD OF THE INVENTION

The field of the invention is sample analysis. The invention concerns other more particular fields, including but not limited to nondestructive testing and evaluation of physical properties of materials.

BACKGROUND OF THE INVENTION

Various techniques are known for conducting non-destructive inspection of structures having a surface area. In one known technique, monochromatic, phase coherent electromagnetic radiation in the 5–50 GHz frequency range (i.e., microwaves) is used for nondestructive testing of dielectric materials. A portion of the impinged beam is combined with the signal reflected by the specimen being inspected. The signals combine to produce an interference pattern, a pattern that changes as the specimen changes, or as the position of the specimen changes relative to that of the detector.

In another known technique, a near-field microwave microscope including a dielectric resonator is used. The microwave microscope has a resonant slit in the conductive end of a microwave waveguide that forms a probe tip. A short dielectric rod is fit into the microwave waveguide near its conductive end. A longer dielectric rod is placed in back of the short dielectric rod with a small gap between the two rods. The length of the shorter rod and the size of the gap are chosen to form a dielectric resonator at the microwave frequency adjacent to the probe tip.

Yet another known testing technique uses a near-field sensor including circuitry which removes variation in the "standoff distance" (i.e., the distance of the sensor from the inspected object) as a factor in the inspection system readings. An original output voltage which varies linearly according to the standoff distance is modified and added to a counterbalancing output voltage which equivalently but oppositely varies linearly according to the standoff distance, resulting in a constant output voltage regardless of the standoff distance.

SUMMARY OF THE INVENTION

The present invention involves an apparatus for inspecting a sample for defects. The apparatus includes a signal generator for generating a signal and a device for splitting the signal into two separate signals which have substantially equal phases and magnitudes. A sensor radiates the two signals on the sample and receives the two signals reflected from the sample. A device is provided for determining a difference between the two signals reflected from the sample without unwanted influence of variations of distance between the sensor and sample, and reflections from nearby sample edges and boundaries. A defect is determined to exist when a difference is found between the two reflected signals.

DETAILED DESCRIPTION OF THE PREFERRED EMBODIMENTS

In the present invention, two coherent electromagnetic signals such as, for example, microwave or millimeter wave signals having substantially identical phase and magnitude are provided from a single generating source and transmitted to a sensor having dual probes. The sensor transmits these signals to a sample under inspection, and receives the signals reflected from the sample. The difference in the reflected signals indicates the presence of a defect in the sample.

The use of dual probes provides for increased sensitivity of the inspection technique and probability of detection of defects. An electrical distance between two apertures of the dual probes provides for removing or significantly reducing unwanted variations or fluctuations in the reflected signals, which could mask the desired reflected signals. These variations or fluctuations may result from variations in the standoff distance caused by, for example, sample surface roughness, sample curvature, scanning platform fluctuations, presence of nearby sample edges and boundaries, etc. In another example, the unwanted variations or fluctuations in reflected signals may be the result of fluctuations in temperature, instability of the source frequency and/or power.

Figure 1:
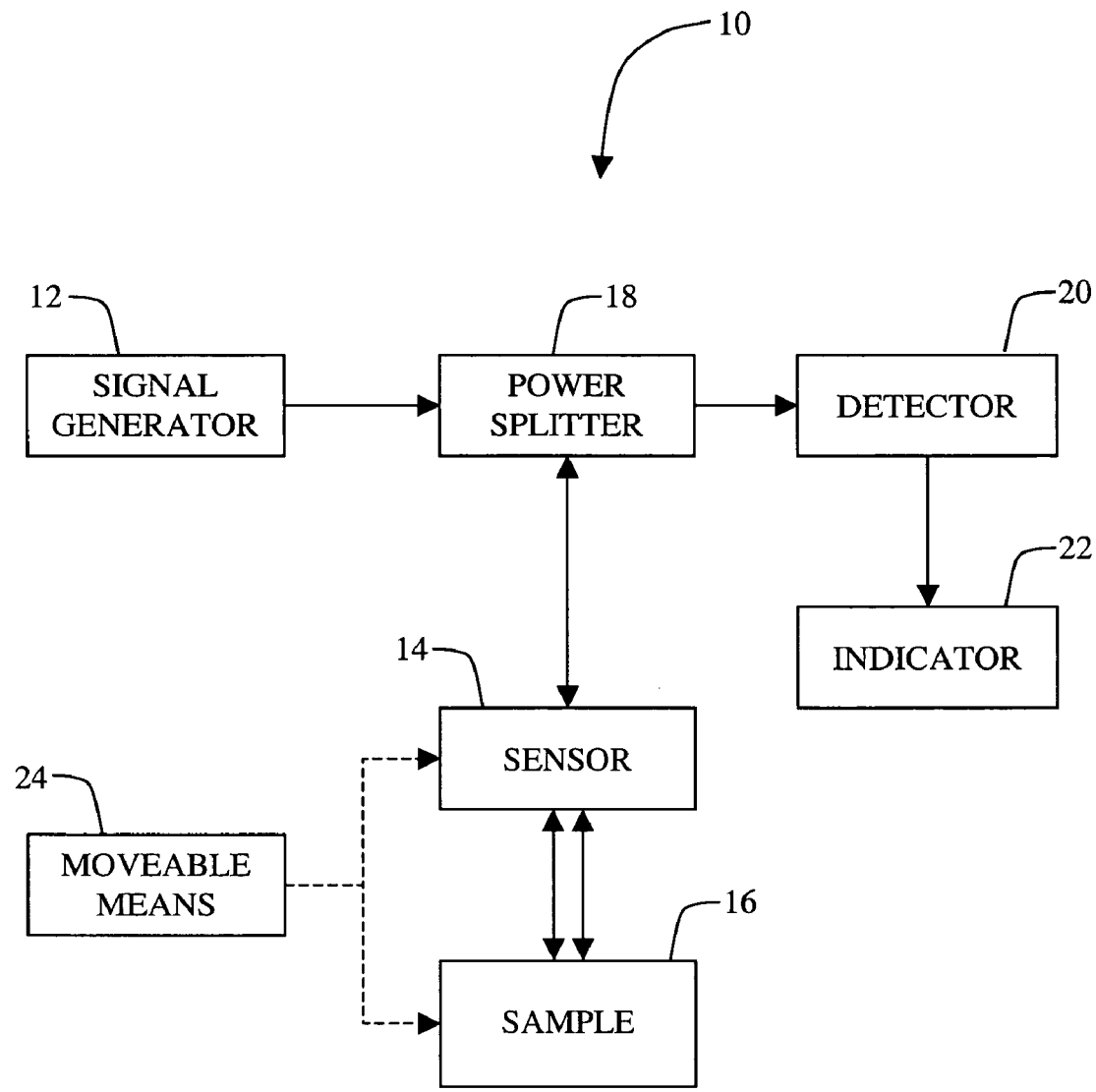
FIG. 1 is a block diagram of the testing system in accordance with one embodiment of the present invention.

Turning now to FIG. 1, a nondestructive testing system 10 in accordance with the present invention includes a signal generator 12, a sensor 14 for radiating signals from the generator 12 to a sample 16 under inspection and for receiving signals reflected from the sample. The testing system 10 also includes a power splitter 18 for dividing a single signal from the signal generator 12 into two separate signals, and obtaining the difference, if any, of the two signals after being reflected from the sample 16. A detector 20 quantifies the difference in the two reflected signals obtained by the power splitter 18. An indicator 22 such as a voltmeter, an oscilloscope or a computer provides a visible indication of the signal difference quantified by the detector 20. The sample 16 and/or the sensor 14 are connected to a position controller 24, e.g., a scanning platform, for exposing the desired areas of the sample 16 to the sensor 14 at a desired standoff distance.

Figure 2:
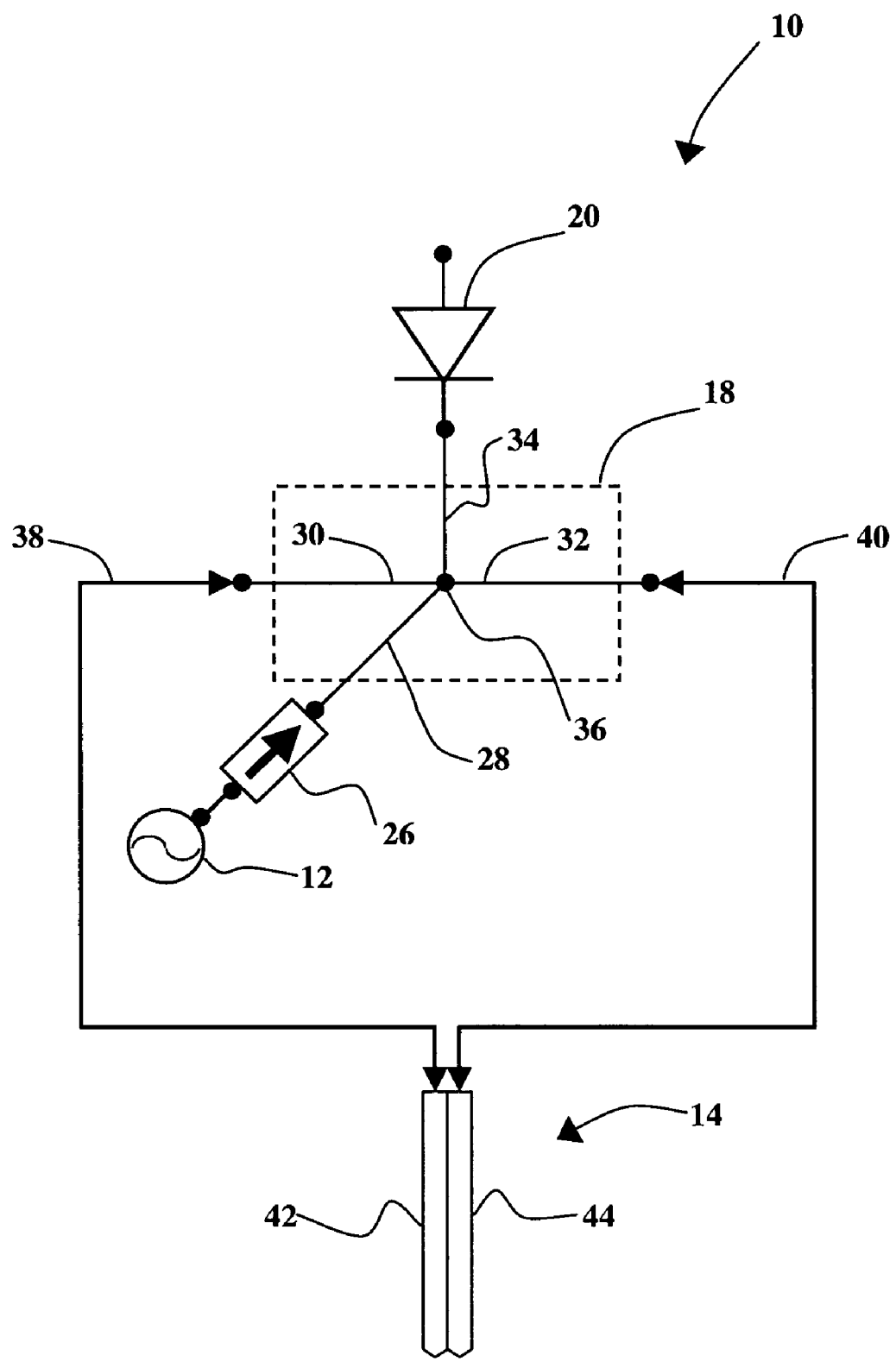
FIG. 2 is a schematic diagram of one embodiment of the testing system shown in FIG. 1.

Referring to FIG. 2 and in accordance with one embodiment of the testing system 10, the signal generator 12 is an oscillator for generating electromagnetic energy, for example, radio frequency (RF), microwave or millimeter wave energy at the desired operating frequency. A signal from the generator 12 goes through an isolator 26, which is a device for allowing the signal to transmit forward, but very little reflected signal to be retransmitted into the signal generator. The isolator 26 protects the signal generator 12 from unwanted reflected signals, which may cause unacceptable source power and frequency instability.

The isolator 26 is connected to the power splitter 18, which in this embodiment is a hybrid tee (also known as a magic tee). The power splitter 18 may also be other hybrid devices which divide signals from the generator 12, and obtain the difference in the two signals after being reflected from the sample 16. A magic tee with 30-dB isolation and 0.5-dB balance over the waveguide frequency bandwidth is an example of the power splitter 18. The power splitter 18 includes four arms 28, 30, 32, 34 which come together at a center point 36. Signals sent from the generator 12 through the isolator 26 to the arm 28 are divided by the power splitter 18 into two signals having equal phases and magnitudes. The divided signals are routed into two arms 30, 32 to be transmitted to the sensor 14. The two arms 30, 32 also receive signals that have been reflected from the sample 16. The power splitter 18 combines these reflected signals and obtains the difference in the signals, which is routed in the arm 34.

The arms 30, 32 in the power splitter 18 are connected respectively to two transmission lines 38, 40, which have substantially the same length and cross-sectional dimensions. While a pair of rectangular waveguides serve as the two transmission lines 38, 40 in one embodiment, other types of lines for carrying signals may be used, such as, for example, circular waveguides, coaxial cables, dielectric waveguides, microstrip lines, fiber optic lines, etc.

The transmission lines 38, 40 at the opposite ends from the power splitter 18 are respectively connected to two probes 42, 44, of the sensor 14. The distal ends (the ends closer to the sample 16) of the probes 42, 44 are open, and thus, they are open-ended transmission lines such as open-ended rectangular waveguides, dielectric waveguides, coaxial cables, microstrip lines, fibers optic lines, etc. The probes 42, 44 may also be open-ended tapered transmission lines (for example, rectangular waveguides which narrow gradually toward their ends) or open-ended flared waveguides (for example, horns). The two probes 42, 44 have substantially identical length and dimensions, and in one embodiment, have a rectangular cross-section. It should be understood, however, that the cross-sections of the probes 42, 44 may have other shapes such as, for example, circular, square, elliptical, etc.

The dimensions of the probes 42, 44 vary with the function of the frequency of the signal from the generator 12 and are proportional to the wavelength. As the frequency of the signal increases, the dimensions of the probes 42, 44 decrease. For example, at the wavelengths of approximately 3 centimeters and 1 centimeters (frequency of 10 gigahertz (GHz) and 30 GHz), the cross-section of a typical open-ended rectangular waveguide probe would be approximately 2 centimeters by 1 centimeter and approximately 0.7 centimeters by 0.3 centimeters, respectively. The probes 42, 44 can be any desired length, which, in effect, includes the length of the transmission lines 38, 40 since they also act as waveguides.

The operating frequency (wavelength) and the probe dimensions are selected according to the desired spatial resolution and radiation efficiency of the testing system 10. When operating in the near-field and for the purpose of microwave or millimeter wave imaging, the aperture size of the probe significantly influences the resulting system spatial resolution. For example, open-ended rectangular waveguide probes 42, 44 at frequencies of greater than 10 GHz may be suitable for inspecting samples such as a metal plate for defects in the form of pits larger than 1 millimeters in diameter. However, for aircraft health monitoring and effective maintenance purposes it is necessary to detect smaller pits since detection of smaller pits means the discovery of earlier corrosion initiation. In this type of application, it may be necessary to increase the frequency of the signal to increase the spatial resolution. As the frequency of the signal increases, the physical aperture dimensions of the probes 42, 44 decrease, resulting in higher spatial resolution. A higher spatial resolution may also be achieved at a given signal frequency by utilizing physical reduction of the probe aperture dimensions through tapering of the walls of the probes 42, 44. On the other hand, when operating in the far-field, open-ended flared waveguide such as, for example, horns, may be used as the probes 42, 44 to increase radiation efficiency and directivity (gain) of the probes.

The signals originating from the generator 12 are radiated from openings of the probes 42, 44 and are incident on an area of the sample 16. In the embodiment shown in FIG. 2 for operating in the near-field, the probes 42, 44 are placed wall to wall and both probes are positioned near the sample 16 approximately 2 mm, for example. In this manner, the signals from the probes are incident on substantially the same location areas of the sample surface and the signals incident on the sample 16 reflect back into the same probes 42, 44 from where they were radiated. The distance between the probes 42, 44 may be varied by moving the probes 42, 44 with respect to one another. When the distance between the centers of the probe apertures is equal to multiple halves of operating wavelength, the testing system 10 effectively removes or significantly reduces the influence of unwanted reflected signals that may come from incidental extended discontinuities of the sample (edges, boundaries, etc.) as a result of the inherent cancellation of the two signals appearing at each probe due to the specific distance between the probes (e.g., half of a wavelength).

The reflected signals travel back through their respective probes 42, 44 and the transmission lines 38, 40, and enter the arms 30, 32 of the power splitter 18, where one signal is subtracted from the other (i.e., one is added to the negative of the other through a 180° phase shift caused by the magic tee). The result of the subtraction in the power splitter 18 appears as a signal across the detector 20 which in this embodiment is a device that converts microwave energy to DC signal such as a diode or a power meter, for example. If the two signals reflected from the sample 16 are identically the same, they cancel out to zero, and the detector 20 ideally does not detect any signal. However, a finite signal at the detector 20 (other than minimal signal due to noise, for example) indicates a detection of a defect. The signal detected at the detector 20 can be converted to a user readable form by connecting the detector 20 to an indicator 22 (shown in FIG. 2) such as a voltmeter, an oscilloscope or a computer.

In the embodiment of the present invention shown in FIG. 2, the paths of the signals generated by the signal generator 12 from the power splitter 18 to the ends of the probes 42, 44 are bi-directional, so that the signals being transmitted to, and being reflected back from, the sample 16 are propagating simultaneously. In this manner, signals from the generator 12 are generated and transmitted continuously as long as necessary to scan the sample 16.

As a way of example, the present invention may be used in inspecting a sample such as a metal plate for anomalies or defects in the form of microscopic corrosion pits, which can grow and become visible corrosion under the paint in a car, for instance. In the aircraft industry, detection of corrosion pits aid in predicting where the corrosion is going to occur. A defect such as a corrosion pit causes the signal radiated on the sample 16 to change in phase and/or magnitude. Therefore, a difference in the phase and/or magnitude of the two signals reflected from the sample indicates the presence of a defect.

In operation, the position controller 24 (shown in FIG. 1) continuously moves the sample 16 or the sensor 14 so that if a defect is present, it would first reach the one of the two probes 42, 44 and then the other one a moment later. The signal reflected from the probes 42 or 44 that first encountered the defect would be different in phase and/or in magnitude from the signal reflected from the other probe which has not yet reached the defect. When the two reflected signals are combined and subtracted in the power splitter 18, a finite (e.g., non-zero) signal (without unwanted influence of standoff distance variation, incidental extended discontinuities of the sample, temperature variation, and frequency and power non-stability of the source) would be obtained. Accordingly, some DC signal drop would appear across the detector 20, indicating that a defect has been found.

Figure 3:
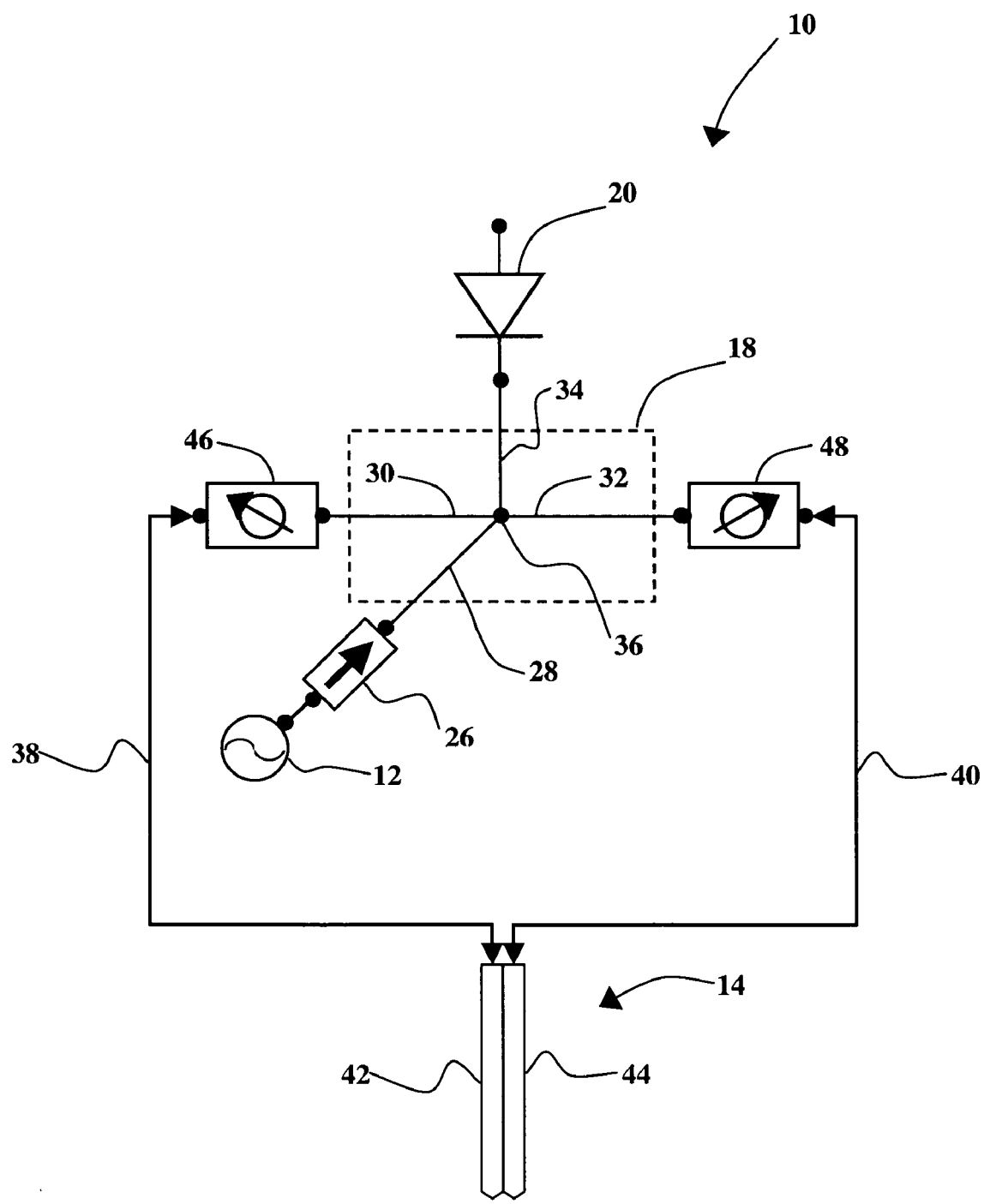
FIG. 3 is a schematic diagram of another embodiment of the testing system shown in FIG. 1.

Turning now to FIG. 3, and in accordance with another embodiment of the invention, the testing system 10 includes a variable phase shifter 46 connected between the arm 30 of the power splitter 18 and the transmission line 38, and another variable phase shifter 48 connected between the arm 32 of power splitter 18 and the transmission line 40. The phase shifters 46, 48 adjust the phase of one or both signals that come out of the power splitter 18, so that they have substantially equal phases when the signals are radiated onto the sample 16. The phase shifters 46, 48 may be required, for example, when the total distance from the power splitter 18 to the ends of the two waveguides 42, 44 are not equal, resulting in the two signals having different phases. The phase shifters 46, 48 are controlled to balance the two signals output from the power splitter 18. The phase shifters 46, 48 may be typical variable phase shifters, for example, rotary vane phase shifters, or simple rectangular waveguides with internal moveable dielectric insertions.

Figure 4:
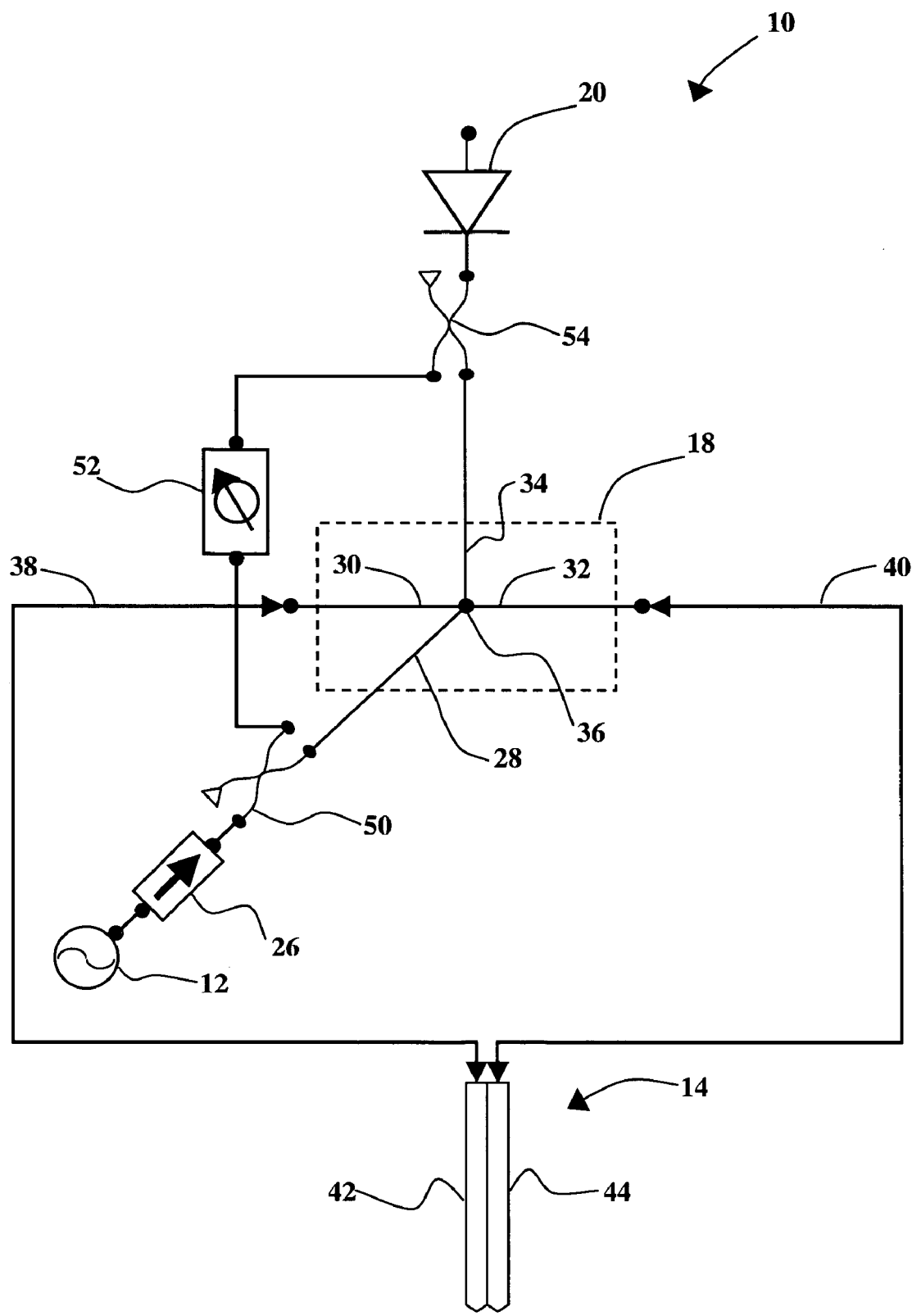
FIG. 4 is a schematic diagram of a further embodiment of the testing system shown in FIG. 1.

In FIG. 4, another embodiment of the testing system 10 includes a directional coupler 50 connected between the isolator 26 and a variable phase shifter 52 connected to the arm 28 of the power splitter. 18, another directional coupler 54 connected between the arm 34 and the detector 20, and a variable phase shifter 52 connected between the direction couplers 50, 54. The variable phase shifter 52 may be a rotary vane phase shifters, or simple rectangular waveguides with internal moveable dielectric insertions, for example. While FIG. 4 does not show the variable phase shifters 46, 48 being included in the testing system 10, the directional couplers 50, 54 may be incorporated in the testing system with or without the phase shifters. Directional couplers 50, 54 with 10-dB coupling and 20-dB directivity or higher over the transmission line bandwidth are examples of couplers that are suitable for use in this embodiment of the invention.

In operation, the coupler 50 routes part of the signal produced by the generator 12 to the coupler 54. The phase shifter 52 provides this part of the signal to be in phase with the difference between the two signals reflected from the sample 16 before being input to the detector 20. In this manner, the couplers 50, 54 and phase shifter 52 supply the detector 20 with some extra power or bias. For example, the signal coming out of the arm 34 of the power splitter 18 may be in the range of approximately 0 milliwatt (if no defect is found) to about 5 milliwatts (if a defect is detected). Even at 5 milliwatts, the signal will not provide for operating of the detector 20 such as a square law diode in optimal linear region and will only result in approximately 2 millivolt drop at the detector 20, making it difficult to accurately read the results of the inspection. By inserting the couplers 50, 54 and the phase shifter 52 in the testing system 10, the detector will be biased at its square law region and smaller input signals will be better detected.

Figure 5:
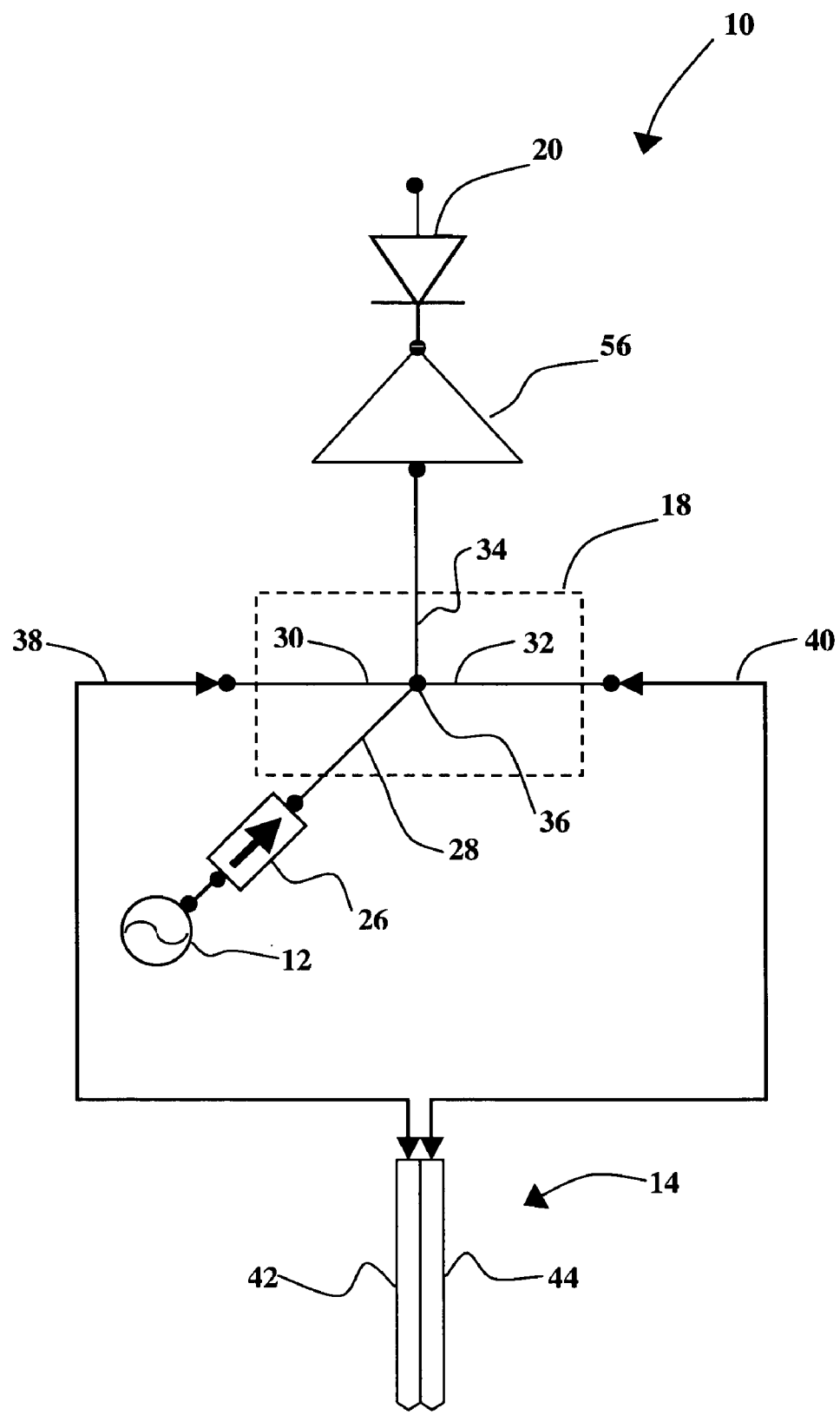
FIG. 5 is a schematic diagram of yet another embodiment of the testing system shown in FIG. 1.

In FIG. 5, another embodiment of the system 10 includes a signal amplifier 56 connected between the arm 34 of the power splitter 18 and the detector 20. The signal amplifier 56 is an amplifier for amplifying electromagnetic energy, for example, microwave or millimeter wave energy at the operating frequency of the signal generator 12. A solid state microwave or millimeter wave low noise amplifier with 10–20 dB gain is an example of the signal amplifier 56. In operation, the amplifier 56 amplifies the signal obtained from taking the difference between the two signals reflected from sample 16 before being input to the detector 20. While FIG. 5 does not show the variable phase shifters 46, 48 (shown in FIG. 3) being included in the testing system 10, the signal amplifier 56 may be incorporated in the testing system with or without the phase shifters 46, 48.

Figure 6:
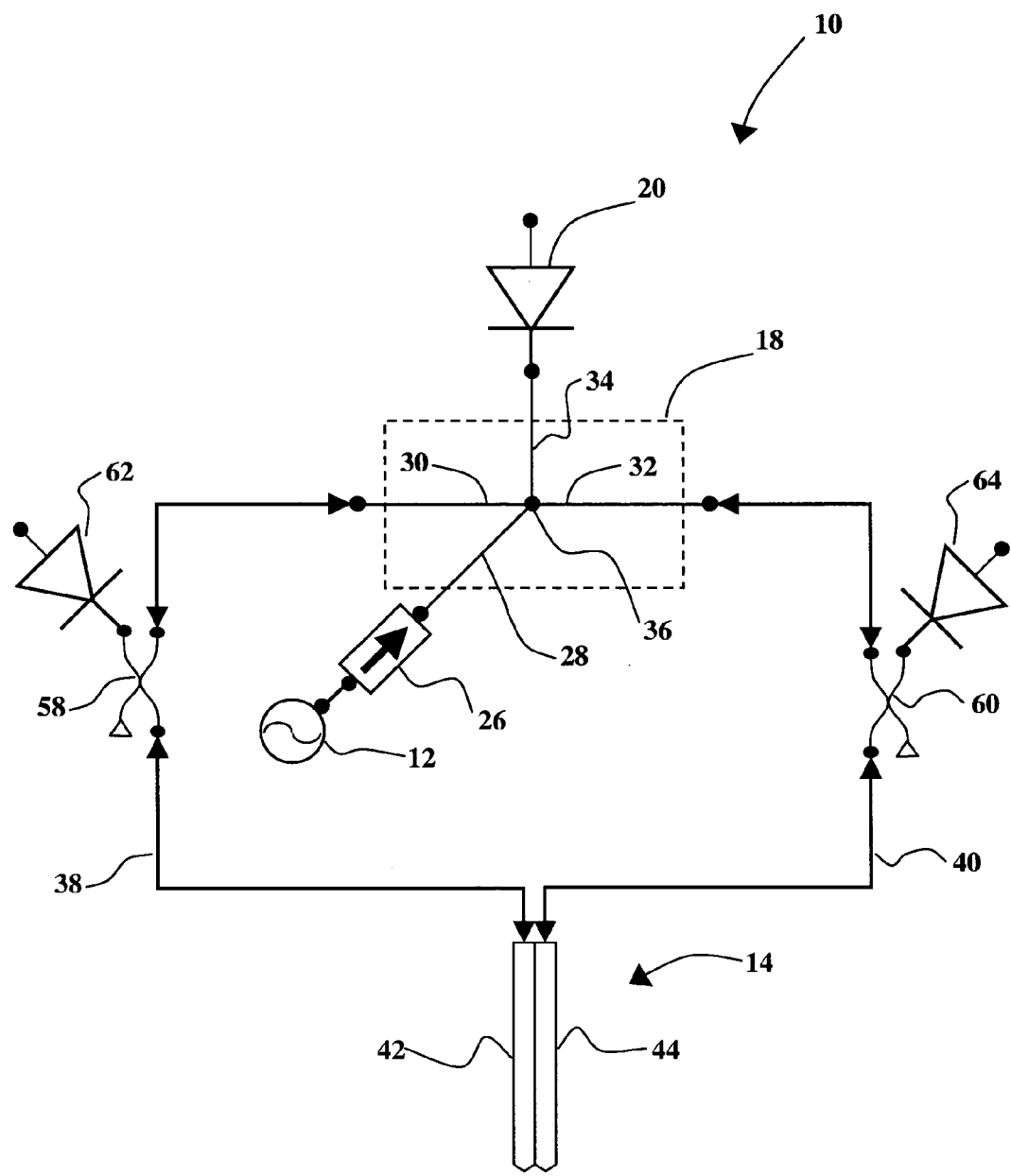
FIG. 6 is a schematic diagram of still another embodiment of the testing system shown in FIG. 1.

Turning now to FIG. 6, and in accordance with another embodiment of the invention, the testing system 10 includes a directional coupler 58 connected between the arm 30 of the power splitter 18 and the transmission line 38, and another directional coupler 60 connected between the arm 32 of the power splitter 18 and the transmission line 40. The directional couplers 58 and 60 with 10-dB coupling and 20-dB directivity or higher over the transmission line bandwidth are examples of couplers that are suitable for use in this embodiment of the invention. Regardless of the type directional coupler used, both couplers 58 and 60 should be identical to one another and inserted into the same location along their respective transmission lines 38 and 40 (relative at least with respect to the probes 42, 44) so that the difference, if any, between the two reflected signals from the sample 16 are not affected by the insertion of the couplers 58, 60 in the transmission lines 38, 40.

A part of the signal reflected from the sample 16 goes through the directional coupler 58 from the probe 42 to a detector 62, which is a device that converts microwave energy to DC signal such as a diode or a power meter, for example. Similarly, the part of signal reflected from the sample 16 goes through the directional coupler 60 from the probe 44 to a detector 64, which is also a device that converts microwave energy to DC signal such as a diode or a power meter, for example. The signals detected at the detectors 62, 64 can be converted to a user readable form by connecting the detectors 62, 64 to the indicator 22 (shown in FIG. 1), such as a voltmeter, an oscilloscope or a computer. These signals provide increasing probability of defect detection and evaluation. While FIG. 6 does not show the variable phase shifters 46, 48 (shown in FIG. 3) being included in the testing system 10, the directional couplers 58, 60 and the detectors 62, 64 may be incorporated in the testing system along with the phase shifters. The directional couplers 58, 60 and the detectors 62, 64 may also be incorporated in the testing system 10 with or without the directional couplers 50, 54 (shown in FIG. 4). The directional couplers 58, 60 and the detectors 62, 64 may also be incorporated in the testing system 10 with or without the signal amplifier 56 (shown in FIG. 5).

In one embodiment, the position controller 24 (shown in FIG. 1) is a scanning table (not shown), which moves the sensor 14 and the sample 16 with respect to each other to provide a raster or C-scan. As the scanning table moves the sample 16 under the sensor 14, a 2D matrix consisting of DC voltages proportional to the local reflection properties of the sample are produced. These voltages are then processed by the indicator 22, which in this embodiment would be a signal processor such as a computer to generate an image of the scanned area. The indicator 22 may generate one image in the case of the embodiments shown in FIGS. 2–4, where the indictor is connected only to the detector 20, or three images simultaneously for the embodiment shown in FIG. 5, where the indicator 22 would be connected to three detectors 20, 58, 60.

While a specific embodiment of the present invention has been shown and described, it should be understood that other modifications, substitutions and alternatives are apparent to one of ordinary skill in the art. Such modifications, substitutions and alternatives can be made without departing from the spirit and scope of the invention, which should be determined from the appended claims.

Various features of the invention are set forth in the appended claims.

The invention claimed is:

1. An apparatus for inspecting a sample for defects, comprising:
    a signal generator for generating a first signal;
    means for splitting said first signal into a second signal and a third signal, said second and third signals having substantially equal phase and magnitude;
    a sensor for radiating said second and third signals on the sample and receiving said second and third signals reflected from the sample; and
    means for determining a difference between said second and third signals reflected from the sample;
    wherein a defect is determined to exist when said difference is found between said second and third signals reflected from the sample.

2. The apparatus as defined in claim 1, wherein said signal generator comprises an oscillator for generating electromagnetic signals.

3. The apparatus as defined in claim 2, wherein said first signal comprises a microwave, a millimeter wave or an RF signal.

4. The apparatus as defined in claim 1, wherein said first signal splitting means and said difference determining means are incorporated in a power splitter.

5. The apparatus as defined in claim 4, wherein said power splitter comprises a hybrid tee.

6. The apparatus as defined in claim 4, wherein said power splitter includes a first arm for receiving said first signal from said signal generator, and a second arm for receiving said difference between said second and third signals reflected from the sample.

7. The apparatus as defined in claim 6, wherein said power splitter further includes a third arm for transmitting said second signal to said sensor and said reflected second signal from said sensor, and a fourth arm for transmitting said third signal to said sensor and said reflected third signal from said sensor.

8. The apparatus as defined in claim 1, further comprising a first transmission line connected between said splitting means and said sensor for transmitting said second signal to said sensor and said reflected second signal from said sensor, and a second transmission line connected between said splitting means and said sensor for transmitting said third signal to said sensor and said reflected third signal from said sensor.

9. The apparatus as defined in claim 8, wherein said first transmission line and said second transmission line have substantially equal length and dimensions.

10. The apparatus as defined in claim 9, wherein said first and second transmission lines are rectangular waveguides, circular waveguides, coaxial cables or dielectric waveguides.

11. The apparatus as defined in claim 8, further including a first phase shifter connected to said first transmission line for adjusting a phase of said second signal, and a second phase shifter connected to said second transmission line for adjusting a phase of said third signal.

12. The apparatus as defined in claim 11, wherein said first and second phase shifters are rotary vane phase shifters or rectangular waveguides with internal moveable dielectric insertions.

13. The apparatus as defined in claim 8, further including a first coupling device electrically connected to said first transmission line for directing a part of said second reflected signal to a first signal detector, and a second coupling device electrically connected to said second transmission line for directing a part of said third reflected signal to a second signal detector, wherein said first signal detector detects voltage proportional to said second reflected signal and said second signal detects a voltage proportional to said third reflected signal.

14. The apparatus as defined in claim 1, wherein said sensor comprises a first probe for radiating said second signal on the sample and receiving said second signal reflected from said sample, and a second probe for radiating said third signal on the sample and receiving said third signal reflected from said sample.

15. The apparatus as defined in claim 14, wherein said first and second probes are open-ended transmission lines having substantially identical dimensions.

16. The apparatus as defined in claim 15, wherein said first and second probes have a cross section which is substantially rectangular, circular or elliptical.

17. The apparatus as defined in claim 1 further comprising a signal detector connected to said difference determining means for obtaining a signal indicating said difference between said reflected second and third signals.

18. The apparatus as defined in claim 17, wherein said signal detector is a diode or a power meter.

19. The apparatus as defined in claim 17, further comprising a first coupling device electrically connected to said signal generator, and a second coupling device electrically connected to said signal detector, wherein said first coupling device is operatively connected to said second coupling device for channeling a part of said first signal to said signal detector.

20. The apparatus as defined in claim 19, further comprising a phase shifter connected between said first and second coupling devices for adjusting said part of said first signal, to be in phase with said signal indicating said difference between said reflected second and third signals.

21. The apparatus as defined in claim 17, further comprising a signal amplifier connected between said difference determining means and said signal detector for amplifying said difference between said reflected second and third signals.

22. The apparatus as defined in claim 21, wherein said signal amplifier is a microwave or millimeter wave amplifier.

23. The apparatus as defined in claim 17 further comprising an indicator electrically connected to said signal detector for visually indicating said difference between said reflected second and third signals.

24. The apparatus as defined in claim 23, wherein said indicator is a voltmeter or an oscilloscope.

25. The apparatus as defined in claim 23, wherein said indicator comprises a computer connected to a position controller for generating an image of said desired area of said sample.

26. The apparatus as defined in claim 1, further comprising a position controller operatively connected to at least one of said sample and said sensor for exposing a desired area of said sample to said sensor.

27. The apparatus as defined in claim 1 further comprising an isolator connected between said signal generator and said splitting means for guiding said first signal into said splitting means and preventing second and third signals from entering said signal generator.

28. A method for inspecting a sample for defects, comprising:
  generating a first signal and a second signal having substantially equal phase and magnitude;
  radiating said first and second signals on the sample; and
  determining a difference between said first and second signals reflected from the sample;
  wherein a defect is determined to exist when said difference is found between said first and second signals reflected from the sample.

29. The method as defined in claim 28, further comprising generating a source signal and splitting said source signal to generate said first and second signals.

30. The method as defined in claim 28 further comprising converting said difference between said first and second signals reflected from the sample to a DC signal.

31. The method as defined in claim 27 further comprising adding a part of said source signal to said difference between said first and second signals reflected from the sample to amplify said difference.

32. The method as defined in claim 28, wherein first and second signals are radiated on and received from the sample using first and second open-ended transmission lines having substantially identical dimensions.

33. The method as defined in claim 32, wherein said first and second signals radiated on, and reflected from, the sample are transmitted to and from said first and second open-ended transmission lines using first and second transmission lines having substantially equal length and dimensions.

34. The method as defined in claim 28, further comprising adjusting the phase of at least one of said first and second signals to make the phases of said first and second signals substantially equal.

35. The method as defined in claim 28, further comprising dividing at least one of said first reflected and second reflected signals into two parts, and converting one of said two parts to a DC signal to obtain a DC signal proportional to said at least one of said first and second reflected signals.

36. The method as defined in claim 28, further comprising moving said sample or sensor to expose a desired area of said sample to said first and second signals.

37. The method as defined in claim 28, further comprising generating an image of said desired area of said sample based on said difference between said first and second reflected signals.

38. The method as defined in claim 28, further comprising amplifying said difference between said first and second signals reflected from the sample.

* * * * *